United States Patent
Huang et al.

(10) Patent No.: US 12,220,710 B2
(45) Date of Patent: Feb. 11, 2025

(54) CONTACTLESS SELECTION DEVICE, LIGHT TRIGGERING STRUCTURE THEREOF, AND BIOLOGICAL PARTICLE SELECTION APPARATUS

(71) Applicant: CYTOAURORA BIOTECHNOLOGIES, INC., Hsinchu County (TW)

(72) Inventors: Chung-Er Huang, Hsinchu County (TW); Sheng-Wen Chen, Hsinchu County (TW); Hsin-Cheng Ho, Hsinchu County (TW)

(73) Assignee: CYTOAURORA BIOTECHNOLOGIES, INC., Hsinchu County (TW)

( * ) Notice: Subject to any disclaimer, the term of this patent is extended or adjusted under 35 U.S.C. 154(b) by 527 days.

(21) Appl. No.: 17/693,440

(22) Filed: Mar. 14, 2022

(65) Prior Publication Data

US 2023/0226558 A1  Jul. 20, 2023

(30) Foreign Application Priority Data

Jan. 18, 2022  (TW) .................................. 111101916

(51) Int. Cl.
  *B03C 5/00*  (2006.01)
  *B01L 3/00*  (2006.01)
  *C12M 1/00*  (2006.01)
  *C12M 1/26*  (2006.01)
  *G02F 1/167*  (2019.01)

(52) U.S. Cl.
  CPC ............ *B03C 5/005* (2013.01); *B01L 3/5027* (2013.01); *C12M 33/00* (2013.01); *C12M 41/06* (2013.01); *C12M 47/04* (2013.01); *G02F 1/167* (2013.01)

(58) Field of Classification Search
  CPC ...... B03C 5/005; B01L 3/5027; C12M 33/00; C12M 41/06; C12M 47/04; G02F 1/167
  See application file for complete search history.

(56) References Cited

U.S. PATENT DOCUMENTS

| 2014/0008230 A1* | 1/2014 | Chen ...................... B03C 5/024 204/643 |
| 2021/0054454 A1* | 2/2021 | Almogy ............ B01L 3/502715 |

FOREIGN PATENT DOCUMENTS

| CN | 111760600 A | * 10/2020 | ........ B01L 3/502707 |
| CN | 113046223 A | * 6/2021 | ........ B01L 3/502715 |
| WO | WO-2007037341 A1 | * 4/2007 | ......... G01N 33/5438 |

* cited by examiner

Primary Examiner — Michelle M Iacoletti
Assistant Examiner — Joshua M Carlson
(74) Attorney, Agent, or Firm — Li & Cai Intellectual Property Office

(57) ABSTRACT

A contactless selection device, a light triggering structure thereof, and a biological particle selection apparatus are provided. The light triggering structure includes a first substrate, a first electrode layer formed on the first substrate, a photodiode layer formed on the first electrode layer, and an insulating layer that covers the photodiode layer. The photodiode layer has a thickness within a range from 1 μm to 3 μm, and includes a first doped layer, an I-type layer, and a second doped layer, which are sequentially stacked from the first electrode layer. The second doped layer includes a plurality of triggering pads spaced apart from each other. Each of the triggering pads has a width within a range from 3 μm to 7 μm, and a distance between any two of the triggering pads adjacent to each other is less than or equal to 2 μm.

20 Claims, 16 Drawing Sheets

CONTACTLESS SELECTION DEVICE, LIGHT TRIGGERING STRUCTURE THEREOF, AND BIOLOGICAL PARTICLE SELECTION APPARATUS

CROSS-REFERENCE TO RELATED PATENT APPLICATION

This application claims the benefit of priority to Taiwan Patent Application No. 111101916, filed on Jan. 18, 2022. The entire content of the above identified application is incorporated herein by reference.

Some references, which may include patents, patent applications and various publications, may be cited and discussed in the description of this disclosure. The citation and/or discussion of such references is provided merely to clarify the description of the present disclosure and is not an admission that any such reference is "prior art" to the disclosure described herein. All references cited and discussed in this specification are incorporated herein by reference in their entireties and to the same extent as if each reference was individually incorporated by reference.

FIELD OF THE DISCLOSURE

The present disclosure relates to a selection device, and more particularly to a contactless selection device, a light triggering structure thereof, and a biological particle selection apparatus.

BACKGROUND OF THE DISCLOSURE

A conventional biological particle selection device can drive a target biological particle to move by applying an electric field therearound. However, in order to enable the conventional biological particle selection device to accurately move the target biological particle along a predetermined path without contacting the target biological particle, the conventional biological particle selection device still requires further improvement in this area.

SUMMARY OF THE DISCLOSURE

In response to the above-referenced technical inadequacies, the present disclosure provides a contactless selection device, a light triggering structure thereof, and a biological particle selection apparatus to effectively improve on the issues associated with conventional biological particle selection devices.

In one aspect, the present disclosure provides a biological particle selection apparatus for selecting a target biological particle from a liquid specimen. The biological particle selection apparatus includes a contactless selection device and the alternating current (AC) source. The contactless selection device includes a light triggering structure and a mating structure. The light triggering structure includes a first substrate, a first electrode layer, a photodiode layer, and an insulating layer. The first electrode layer is formed on the first substrate. The photodiode layer is formed on the first electrode layer, and a thickness of the photodiode layer is within a range from 1 µm to 3 µm. The photodiode layer includes a first doped layer, an I-type layer, and a second doped layer. The first doped layer is formed on the first electrode layer. The I-type layer is formed on the first doped layer. The second doped layer includes a plurality of triggering pads that are formed on the I-type layer and that are spaced apart from each other. Moreover, a width of each of the triggering pads is within a range from 3 µm to 7 µm, and a distance between any two of the triggering pads adjacent to each other is less than or equal to 2 µm. The insulating layer covers the photodiode layer. The mating structure is spaced apart from the light triggering structure. At least one of the mating structure and the light triggering structure is transparent, and the mating structure includes a second substrate and a second electrode layer that is formed on the second substrate and that faces toward the light triggering structure. The AC source is electrically coupled to the first electrode layer and the second electrode layer. When the liquid specimen is located between the insulating layer and the second electrode layer of the contactless selection device, the contactless selection device allows a light source to irradiate light onto at least one of the triggering pads so as to generate a concentrated and non-uniform electric field to the liquid specimen for applying a dielectrophoresis (DEP) force on the target biological particle, in which the DEP force is capable of driving movement of the target biological particle.

In another aspect, the present disclosure provides a contactless selection device for selecting a target biological particle from a liquid specimen. The contactless selection device includes a light triggering structure and a mating structure. The light triggering structure includes a first substrate, a first electrode layer, a photodiode layer, and an insulating layer. The first electrode layer is formed on the first substrate. The photodiode layer is formed on the first electrode layer, and a thickness of the photodiode layer is within a range from 1 µm to 3 µm. The photodiode layer includes a first doped layer formed on the first electrode layer, an I-type layer formed on the first doped layer, and a second doped layer including a plurality of triggering pads that are formed on the I-type layer and that are spaced apart from each other. A width of each of the triggering pads is within a range from 3 µm to 7 µm, and a distance between any two of the triggering pads adjacent to each other is less than or equal to 2 µm. The insulating layer covers the photodiode layer. The mating structure is spaced apart from the light triggering structure. At least one of the mating structure and the light triggering structure is transparent, and the mating structure includes a second substrate and a second electrode layer that is formed on the second substrate and that faces toward the light triggering structure. Moreover, a space between the insulating layer and the second electrode layer of the contactless selection device is configured to accommodate the liquid specimen so as to implement a selection process for the target biological particle.

In yet another aspect, the present disclosure provides a light triggering structure of a contactless selection device. The light triggering structure includes a first substrate, a first electrode layer formed on the first substrate, a photodiode layer formed on the first electrode layer, and an insulating layer that covers the photodiode layer. Moreover, a thickness of the photodiode layer is within a range from 1 µm to 3 µm. The photodiode layer includes a first doped layer formed on the first electrode layer and an I-type layer formed on the first doped layer. The I-type layer has a patterned trench recessed therein which forms a plurality of protruding stages spaced apart from each other, and wherein a width of each of the protruding stages is within a range from 3 µm to 7 µm, and a distance between any two of the protruding stages adjacent to each other is less than or equal to 2 µm.

Therefore, the photodiode layer of the biological particle selection apparatus (or the contactless selection device) provided by the present disclosure has a specific structural design (e.g., any two of the triggering pads or the protruding stages adjacent to each other are spaced apart by the distance, and the width of each of the triggering pads or the protruding stages is a predetermined value; or, the transparent electrode pads can be further formed on the triggering pads), so that any one of the triggering pads can be used to generate the concentrated electric field in a contactless photoelectric coupling manner that is similar to a corona discharge, thereby enabling to accurately move (or capture) the target biological particle to any position.

These and other aspects of the present disclosure will become apparent from the following description of the embodiment taken in conjunction with the following drawings and their captions, although variations and modifications therein may be affected without departing from the spirit and scope of the novel concepts of the disclosure.

BRIEF DESCRIPTION OF THE DRAWINGS

The described embodiments may be better understood by reference to the following description and the accompanying drawings, in which.

DETAILED DESCRIPTION OF THE EXEMPLARY EMBODIMENTS

Figure 1:
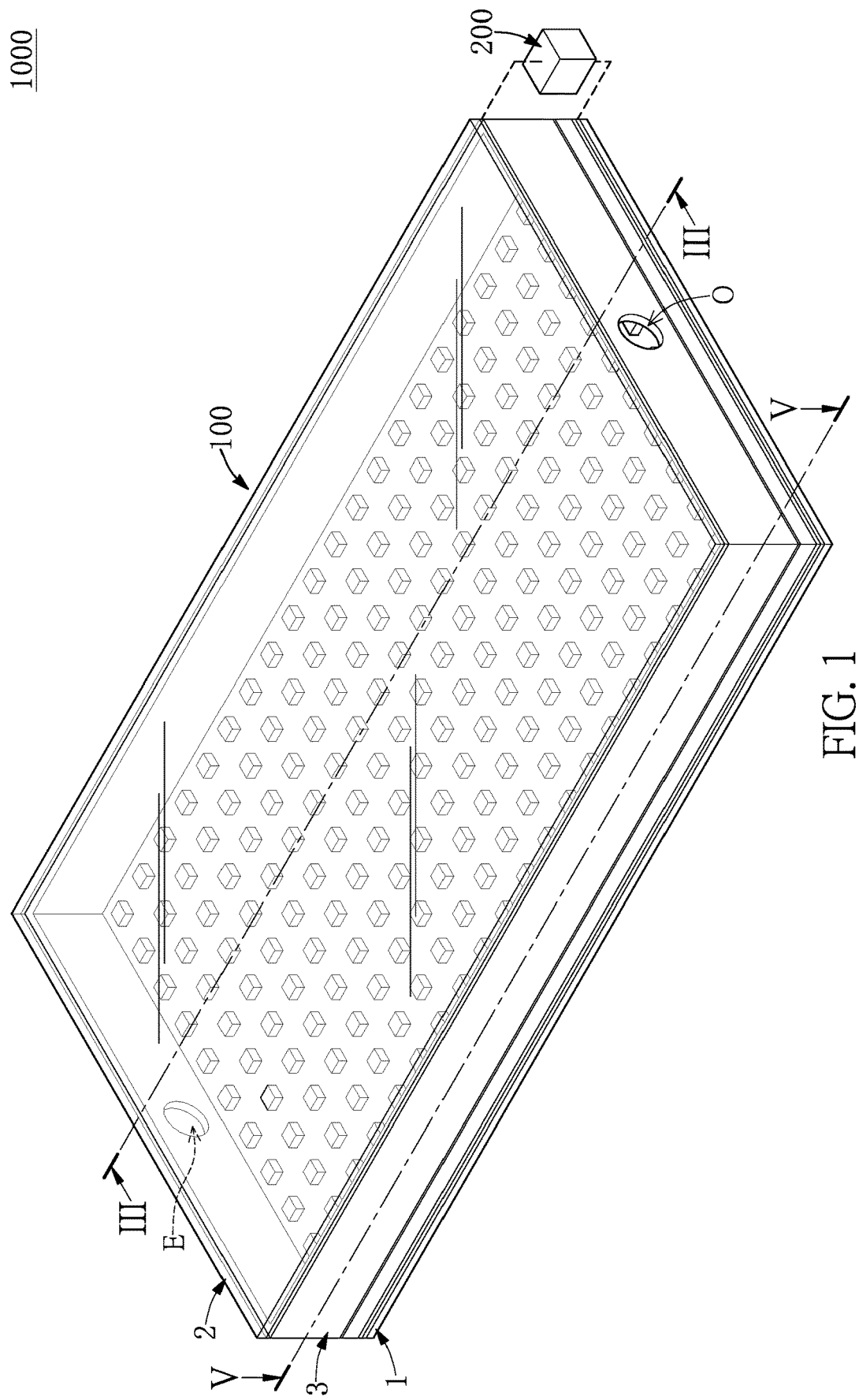
FIG. 1 is a perspective view of a biological particle selection apparatus according to a first embodiment of the present disclosure.

The present disclosure is more particularly described in the following examples that are intended as illustrative only since numerous modifications and variations therein will be apparent to those skilled in the art. Like numbers in the drawings indicate like components throughout the views. As used in the description herein and throughout the claims that follow, unless the context clearly dictates otherwise, the meaning of "a", "an", and "the" includes plural reference, and the meaning of "in" includes "in" and "on". Titles or subtitles can be used herein for the convenience of a reader, which shall have no influence on the scope of the present disclosure.

The terms used herein generally have their ordinary meanings in the art. In the case of conflict, the present document, including any definitions given herein, will prevail. The same thing can be expressed in more than one way. Alternative language and synonyms can be used for any term(s) discussed herein, and no special significance is to be placed upon whether a term is elaborated or discussed herein. A recital of one or more synonyms does not exclude the use of other synonyms. The use of examples anywhere in this specification including examples of any terms is illustrative only, and in no way limits the scope and meaning of the present disclosure or of any exemplified term. Likewise, the present disclosure is not limited to various embodiments given herein. Numbering terms such as "first", "second" or "third" can be used to describe various components, signals or the like, which are for distinguishing one component/signal from another one only, and are not intended to, nor should be construed to impose any substantive limitations on the components, signals or the like.

First Embodiment

Figure 2:
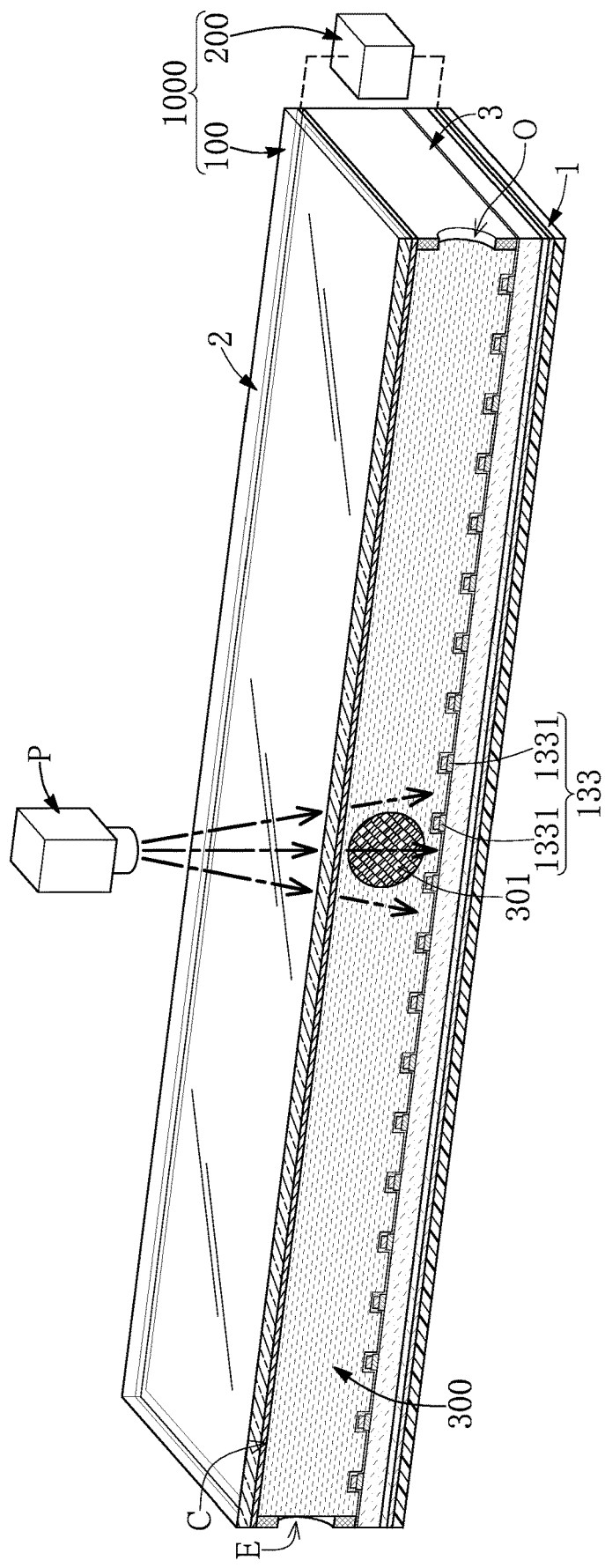
FIG. 2 is a perspective cross-sectional view showing the biological particle selection apparatus of FIG. 1 used to be injected with a liquid specimen.

Referring to FIG. 1 to FIG. 6, a first embodiment of the present disclosure provides a biological particle selection apparatus 1000. As shown in FIG. 1 and FIG. 2, the biological particle selection apparatus 1000 is configured for selecting a target biological particle 301 from a liquid specimen 300. In other words, any selection apparatus not used for a biological particle is different from the biological particle selection apparatus 1000 of the present embodiment.

The liquid specimen 300 can be a body fluid from an animal (e.g., blood, lymph, saliva, or urine), and the target biological particle 301 can be a specific type of cell, such as circulating tumor cells (CTC), fetal nucleated red blood cells (FNRBC), virus, or bacteria, but the present disclosure is not limited thereto. For example, in other embodiments of the present disclosure not shown in the drawings, the liquid specimen 300 can be obtained from plants.

Moreover, the biological particle selection apparatus 1000 in the present embodiment includes a contactless selection device 100 and an alternating current (AC) source 200 (e.g., an AC signal source or an AC power source) that is electrically coupled to the contactless selection device 100, but the present disclosure is not limited thereto. For example, in other embodiments of the present disclosure not shown in the drawings, the contactless selection device 100 can be independently used (e.g., sold) or can be used in cooperation with other devices. The following description describes the structure and connection relationship of each component of the contactless selection device 100, and then describes the connection relationship between the contactless selection device 100 and the AC source 200.

It should be noted that the contactless selection device 100 of the present embodiment is formed in a chip-scale (e.g., a thickness of the contactless selection device 100 is less than or equal to 100 μm), and the contactless selection device 100 shown in the drawings is a rectangular structure, but the present disclosure is not limited thereto. For example, in other embodiments of the present disclosure not shown in the drawings, the contactless selection device 100 can be an irregular structure.

Specifically, the contactless selection device 100 in the present embodiment includes a light triggering structure 1, a mating structure 2 spaced apart from the light triggering structure 1, and a bonding layer 3 that is connected to and located between the light triggering structure 1 and the mating structure 2. In order to clearly describe the contactless selection device 100, the mating structure 2 of the present embodiment is transparent. According to practical requirements, at least one of the mating structure 2 and the light triggering structure 1 can be transparent so as to enable the contactless selection device 100 to be normally operated.

Figure 3:
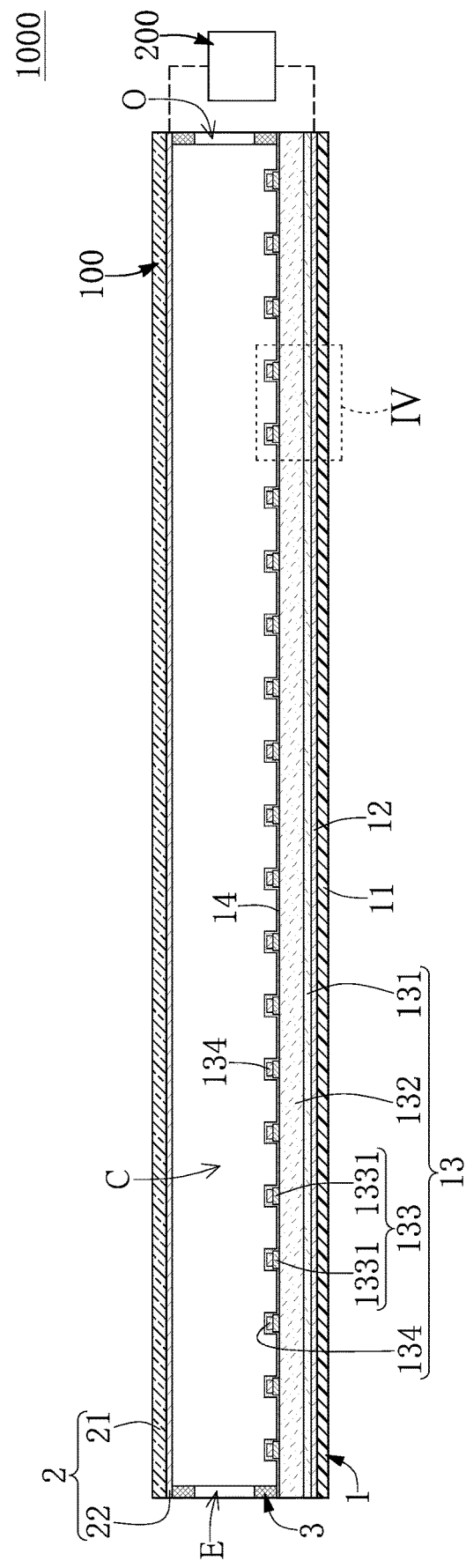
FIG. 3 is a cross-sectional view taken along line III-III of FIG. 1.
Figure 4:
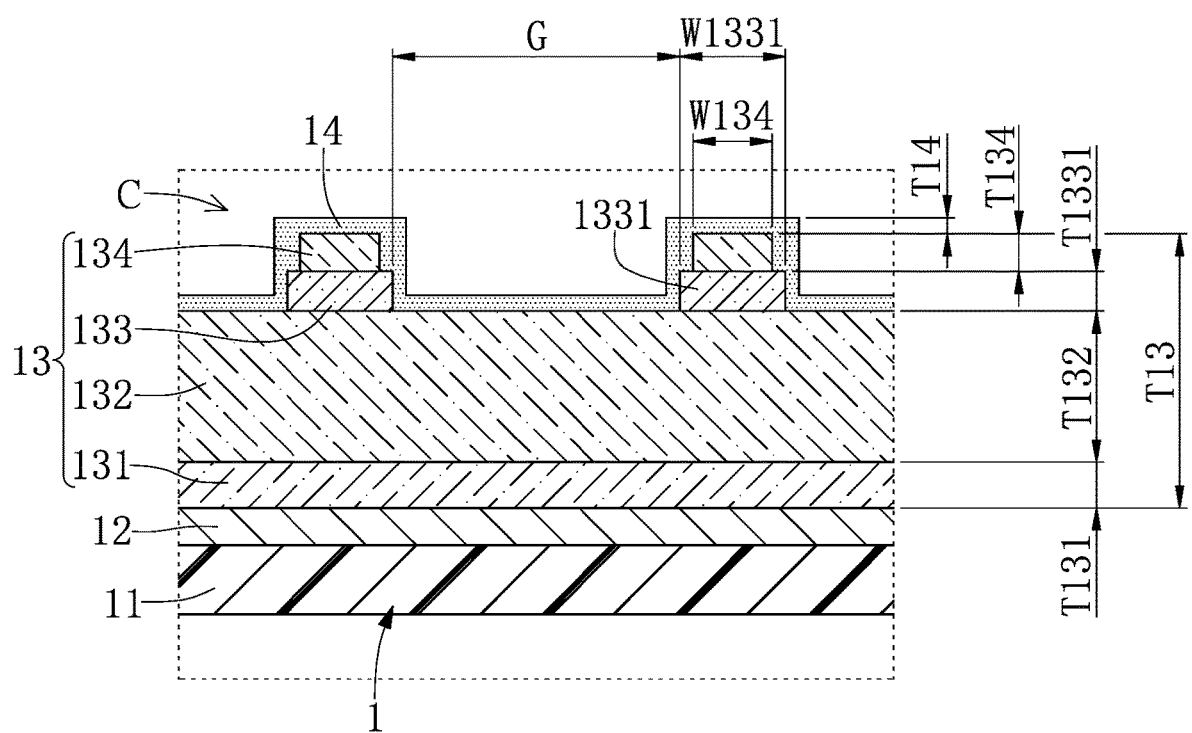
FIG. 4 is an enlarged view of part IV of FIG. 3.
Figure 5:
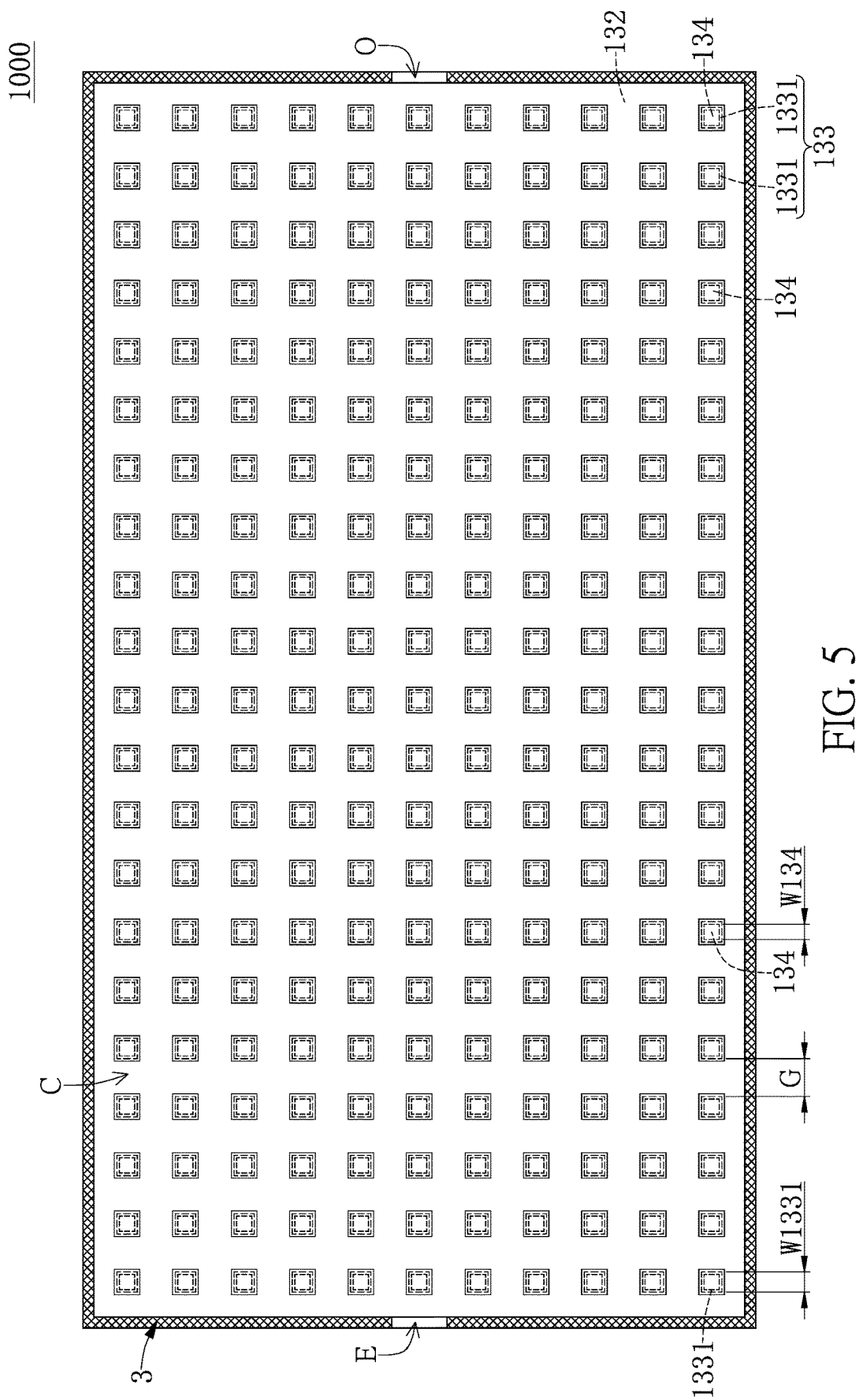
FIG. 5 is a cross-sectional view taken along line V-V of FIG. 1.
Figure 6:
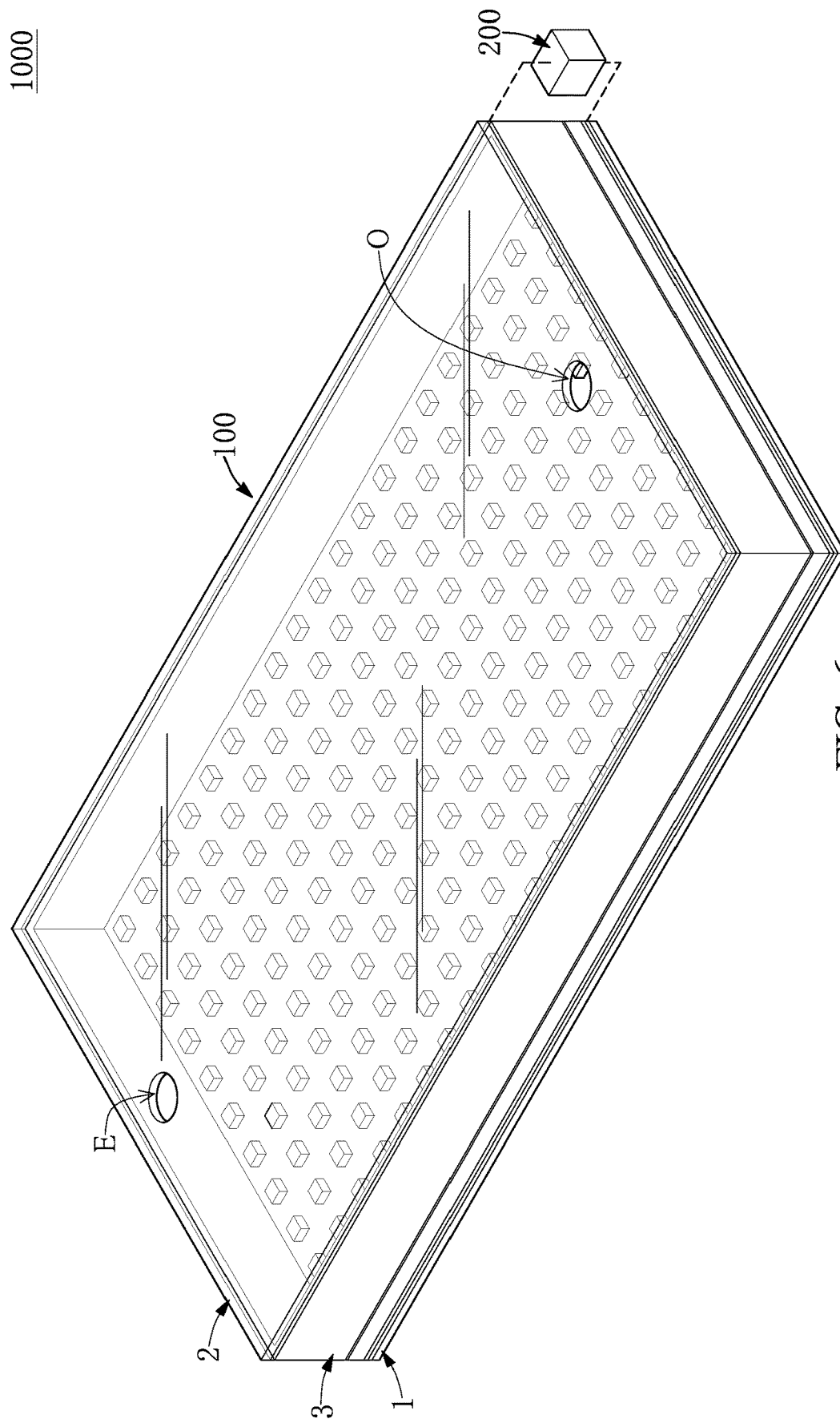
FIG. 6 is a perspective view of the biological particle selection apparatus in another configuration according to the first embodiment of the present disclosure.

As shown in FIG. 2 to FIG. 4, the light triggering structure 1 includes a first substrate 11, a first electrode layer 12 formed on the first substrate 11, a photodiode layer 13 formed on the first electrode layer 12, and an insulating layer 14 that covers the photodiode layer 13. The first electrode layer 12 can cover an entirety of board surface of the first substrate 11, and the photodiode layer 13 is located between the first electrode layer 12 and the insulating layer 14 (e.g., the photodiode layer 13 is embedded in the first electrode layer 12 and the insulating layer 14).

In the present embodiment, the first substrate 11 is a glass board, the first electrode layer 12 is a thin metal layer or an indium tin oxide (ITO) layer, the photodiode layer 13 is a semiconductor layer in a PIN type and has a thickness T13 within a range from 1 μm to 3 μm (e.g., the thickness T13 is about 1.5 μm), and the insulating layer 14 is a silicon nitride layer or a silicon oxide layer and has a thickness T14 within a range from 10 nm to 100 nm.

Specifically, the photodiode layer 13 can include a first doped layer 131 formed on the first electrode layer 12, an I-type layer 132 formed on the first doped layer 131, a second doped layer 133 formed on the I-type layer 132, and a plurality of transparent electrode pads 134 that are formed on the second doped layer 133, but the present disclosure is not limited thereto. For example, in other embodiments of the present disclosure not shown in the drawings, the transparent electrode pads 134 of the photodiode layer 13 can be omitted or can be replaced by other structures according to design requirements.

In the present embodiment, the first doped layer 131 is an N-type layer (e.g., an amorphous silicon layer in heavily doped N-type) deposited on the first electrode layer 12, and the first doped layer 131 preferably covers at least 90% of an area of the first electrode layer 12. The I-type layer 132 is an amorphous silicon layer in lightly doped I-type (or in undoped I-type) deposited on the first doped layer 131, and the I-type layer 132 covers an entirety of the first doped layer 131. In other words, each of the first doped layer 131 and the I-type layer 132 of the present embodiment is in a single sheet-like structure or is a flat layer.

Moreover, the second doped layer 133 is a P-type layer (e.g., an amorphous silicon layer in lightly doped P-type) deposited on the first doped layer 131, the second doped layer 133 includes a plurality of triggering pads 1331 spaced apart from each other, and the transparent electrode pads 134 are respectively formed on the triggering pads 1331. The triggering pads 1331 in the present embodiment are in a regular arrangement (e.g., a matrix arrangement shown in FIG. 5), but the present disclosure is not limited thereto. For example, in other embodiments of the present disclosure not shown in the drawings, the first doped layer 131 can be a P-type layer, and the second doped layer 133 can be an N-type layer.

Specifically, a width W1331 of each of the triggering pads 1331 is within a range from 3 μm to 7 μm, the width W1331 (e.g., 5 μm) of each of the triggering pads 1331 is preferably greater than a width W134 (e.g., 3 μm) of the corresponding transparent electrode pad 134, and a distance G between any two of the triggering pads 1331 adjacent to each other is less than or equal to 2 μm (e.g., the distance G is about 1 μm).

In other words, a thickness T1331 (e.g., 10 nm) of each of the triggering pads 1331 is 3% to 10% of a thickness T134 (e.g., about 200 nm) of the corresponding transparent electrode pad 134. Furthermore, the thickness T1331 of each of the triggering pads 1331 and a thickness T131 of the first doped layer 131 are each 1% to 5% of a thickness T132 (e.g., about 1000 nm) of the I-type layer 132, and the thickness T1331 (e.g., about 10 nm) of each of the triggering pads 1331 is less than the thickness T131 (e.g., about 20 nm) of the first doped layer 131.

It should be noted that when the target biological particle 301 is considered, any slight change in the contactless selection device 100 would have a significant influence on the target biological particle 301. Accordingly, the above description in the present embodiment describes the size and arrangement of each element of the photodiode layer 13 that are provided to facilitate to select the target biological particle 301 under a relatively low external force, but the present disclosure is not limited thereto.

The mating structure 2 includes a second substrate 21 and a second electrode layer 22 that is formed on the second substrate 21 and that faces toward the light triggering structure 1. The bonding layer 3 is connected to and located between the light triggering structure 1 and the mating structure 2 (e.g., the bonding layer 3 connects the insulating layer 14 and the second electrode layer 22), so that the bonding layer 3, the light triggering structure 1, and the mating structure 2 jointly define an accommodating space C. A space (i.e., the accommodating space C) between the insulating layer 14 and the second electrode layer 22 of the contactless selection device 100 is configured to accommodate the liquid specimen 300 so as to implement a selection process for the target biological particle 301.

Specifically, at least one of the mating structure 2 and the bonding layer 3 has an inlet E and an outlet O (shown in FIG. 1 and FIG. 6), which are respectively in spatial communication with two ends of the accommodating space C. The liquid specimen 300 can be injected into the contactless selection device 100 through the inlet E, and can flow out of the contactless selection device 100 through the outlet O.

It should be noted that the light triggering structure 1 of the contactless selection device 100 provided by the present embodiment is in cooperation with the mating structure 2 and the bonding layer 3, but the present disclosure is not limited thereto. For example, in other embodiments of the present disclosure not shown in the drawings, the bonding layer 3 of the light triggering structure 1 can be omitted or can be replaced by other structures; or, the light triggering structure 1 can be independently used (e.g., sold) or can be used in cooperation with other devices.

The AC source 200 is electrically coupled to the first electrode layer 12 and the second electrode layer 22 of the contactless selection device 100. Moreover, when the liquid specimen 300 is located between the insulating layer 14 and the second electrode layer 22 of the contactless selection device 100, the contactless selection device 100 allows a light source P to irradiate light onto at least one of the triggering pads 1331 so as to generate a concentrated and non-uniform electric field to the liquid specimen 300 for applying a dielectrophoresis (DEP) force on the target biological particle 301, in which the DEP force is capable of driving movement of the target biological particle 301.

In summary, the photodiode layer 13 of the biological particle selection apparatus 1000 (or the contactless selection device 100) provided by the present embodiment has a specific structural design (e.g., any two of the triggering pads 1331 adjacent to each other are spaced apart from by the distance G, and the width W1331 of each of the triggering pads 1331 is a predetermined value; or, the transparent electrode pads 134 can be further formed on the triggering pads 1331), so that any one of the triggering pads 1331 can be used to generate the concentrated electric field in a contactless photoelectric coupling manner that is similar to a corona discharge, thereby enabling to accurately move (or capture) the target biological particle 301 to any position.

Second Embodiment

Figure 7:
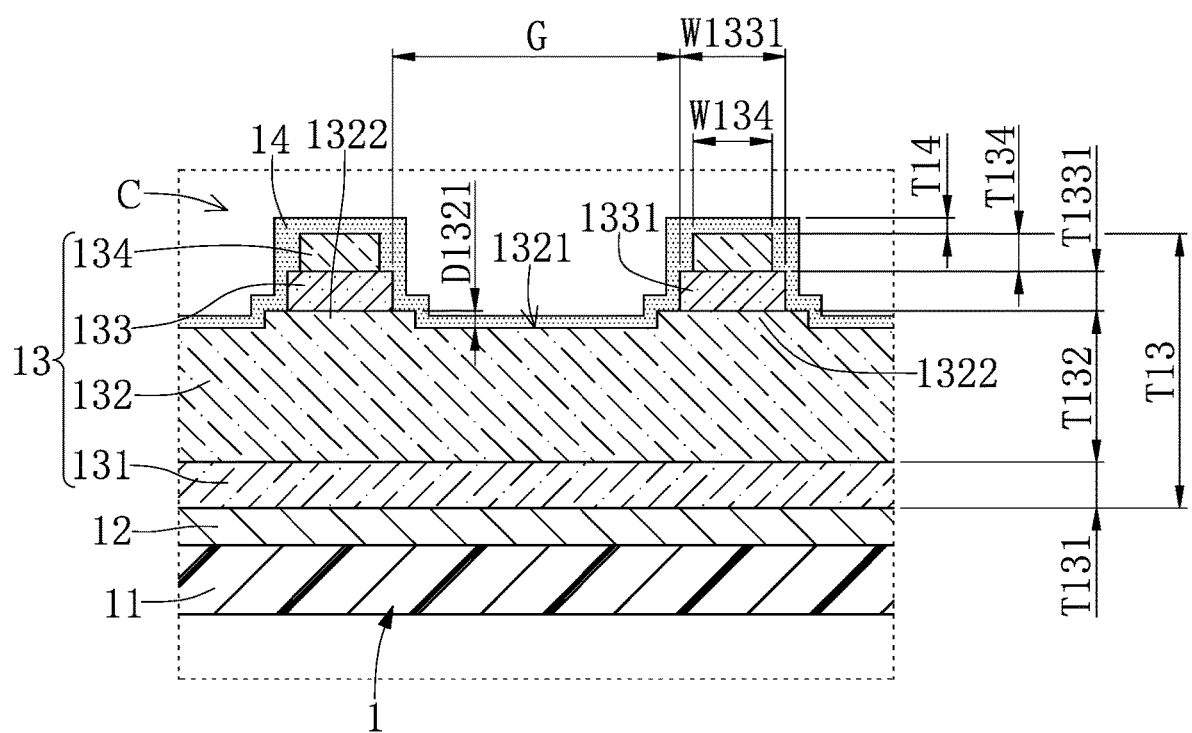
FIG. 7 is an enlarged view of the biological particle selection apparatus according to a second embodiment of the present disclosure.

Referring to FIG. 7, a second embodiment of the present disclosure is provided, which is similar to the first embodiment of the present disclosure. For the sake of brevity, descriptions of the same components in the first and second embodiments of the present disclosure will be omitted herein, and the following description only discloses different features between the first and second embodiments, in which the different features reside in the photodiode layer 13.

In the present embodiment, the I-type layer 132 has a patterned trench 1321 recessed therein which forms a plurality of protruding stages 1322 spaced apart from each other, and the triggering pads 1331 are respectively formed on the protruding stages 1322. Moreover, an edge of each of the triggering pads 1331 is flush with an edge of the corresponding protruding stage 1322, and a depth D1321 (e.g., about 20 nm) of the patterned trench 1321 is 1% to 5% of a thickness T132 of the I-type layer 132.

Third Embodiment

Figure 8:
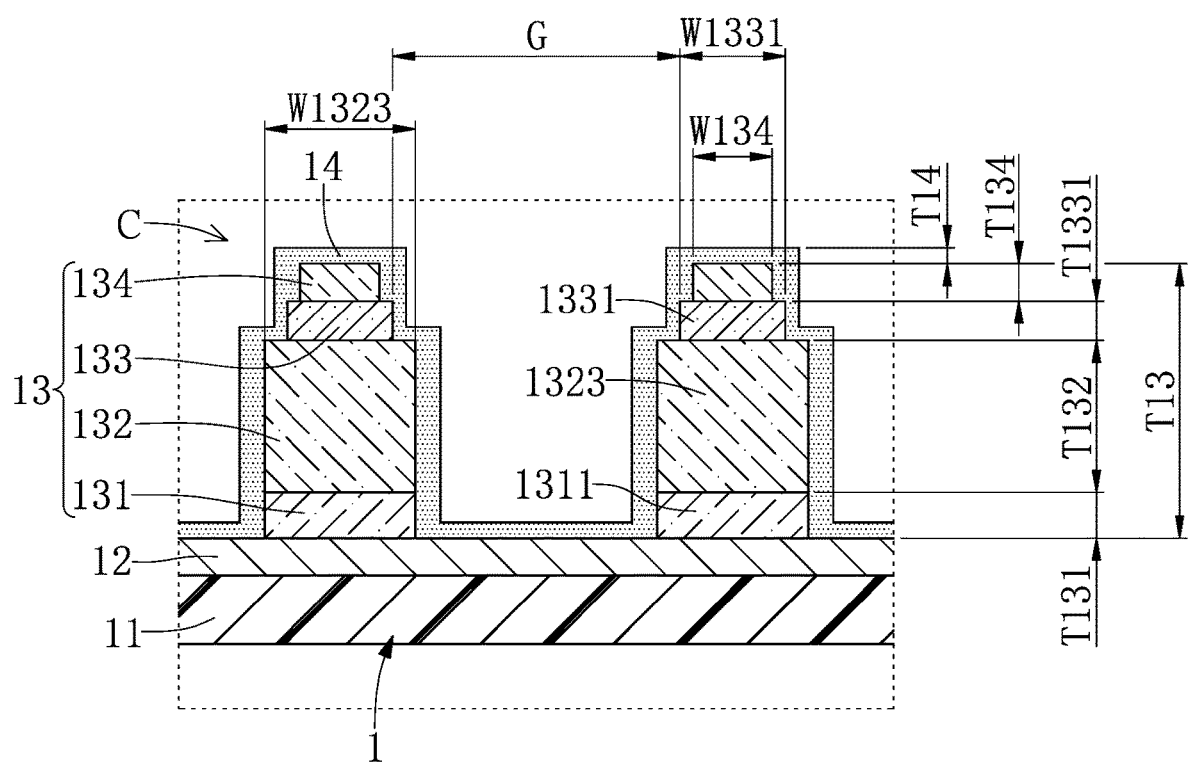
FIG. 8 is an enlarged view of the biological particle selection apparatus according to a third embodiment of the present disclosure.

Referring to FIG. 8, a third embodiment of the present disclosure is provided, which is similar to the first and second embodiments of the present disclosure. For the sake of brevity, descriptions of the same components in the first to third embodiments of the present disclosure will be omitted herein, and the following description only discloses different features among the third embodiment and the first and second embodiments, in which the different features reside in the photodiode layer 13.

In the present embodiment, the I-type layer 132 includes a plurality of I-type pads 1323 that are disposed on the first doped layer 131 and that are spaced apart from each other. The triggering pads 1331 are respectively formed on the I-type pads 1323, and the width W1331 (e.g., about 5 µm) of each of the triggering pads 1331 is less than a width W1323 (e.g., about 10 µm) of the corresponding I-type pad 1323.

Moreover, the first doped layer 131 preferably includes a plurality of spacing pads 1311 that are disposed on the first electrode layer 12 and that are spaced apart from each other. The I-type pads 1323 are respectively formed on the spacing pads 1311, and an edge of each of the I-type pads 1323 is flush with an edge of the corresponding spacing pad 1311, but the present disclosure is not limited thereto. For example, in other embodiments of the present disclosure not shown in the drawings, the I-type layer 132 includes the I-type pads 1323, but the first doped layer 131 is in a single sheet-like structure or is a flat layer that is similar to the corresponding structure shown in the first embodiment. In addition, the thickness of the insulating layer 14 can be adjusted according to design requirements.

Fourth Embodiment

Referring to FIG. 9 to FIG. 13, a fourth embodiment of the present disclosure is provided, which is similar to the first to third embodiments of the present disclosure. For the sake of brevity, descriptions of the same components in the first to fourth embodiments of the present disclosure will be omitted herein, and the following description only discloses different features among the fourth embodiment and the first to third embodiments, in which the different features reside in that the contactless selection device 100 of the present embodiment further includes a plurality of spacing walls 4 that are arranged in the accommodating space C and that are connected to the light triggering structure 1 and the mating structure 2.

Figure 9:
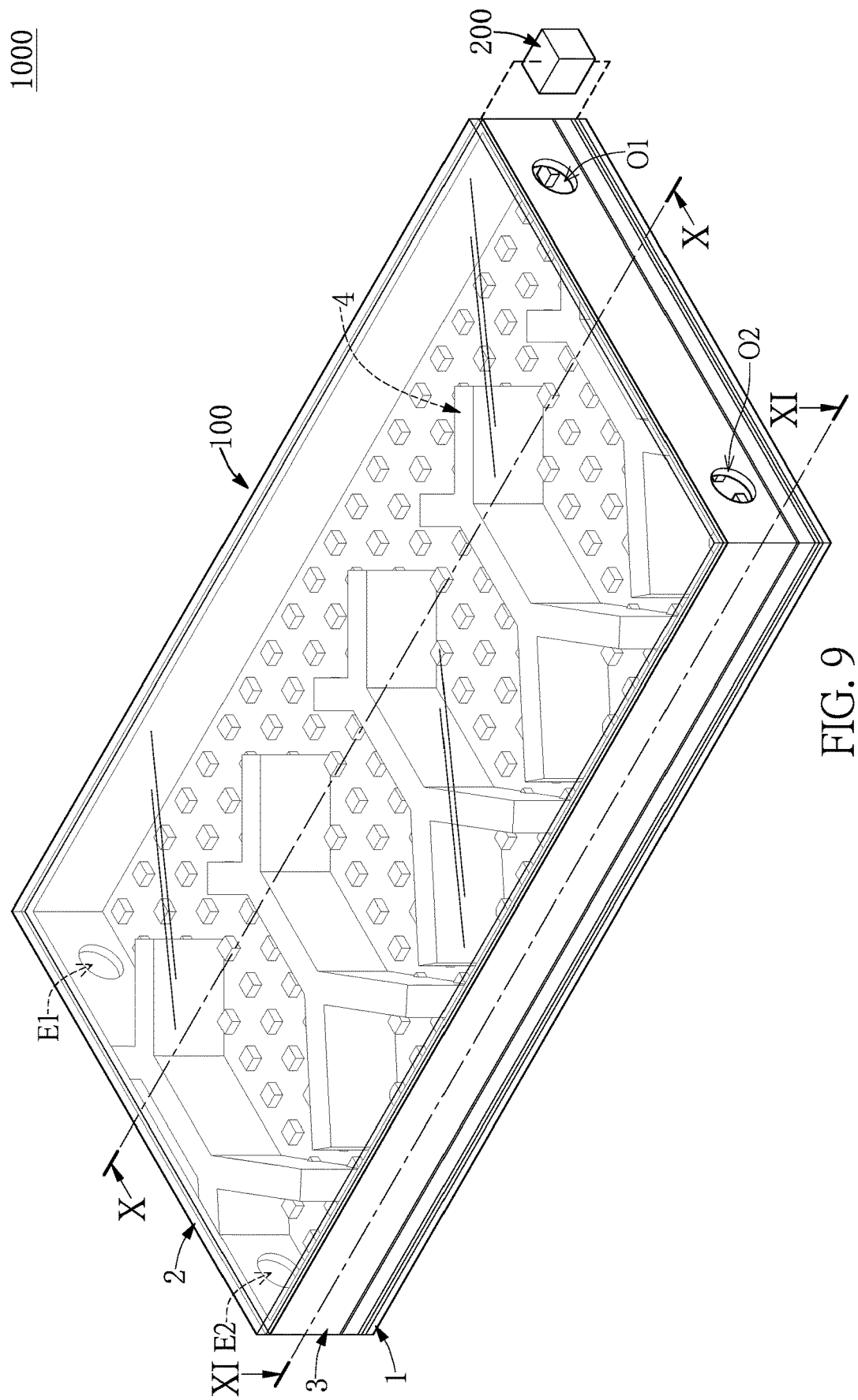
FIG. 9 is a perspective view of the biological particle selection apparatus according to a fourth embodiment of the present disclosure.
Figure 10:
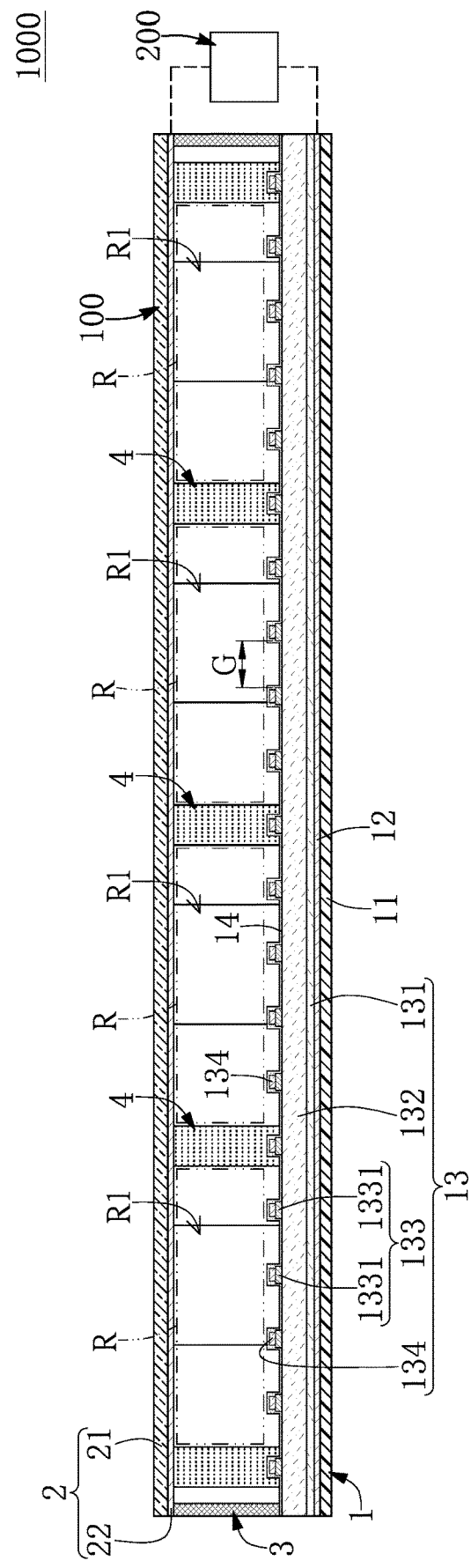
FIG. 10 is a cross-sectional view taken along line X-X of FIG. 9.
Figure 11:
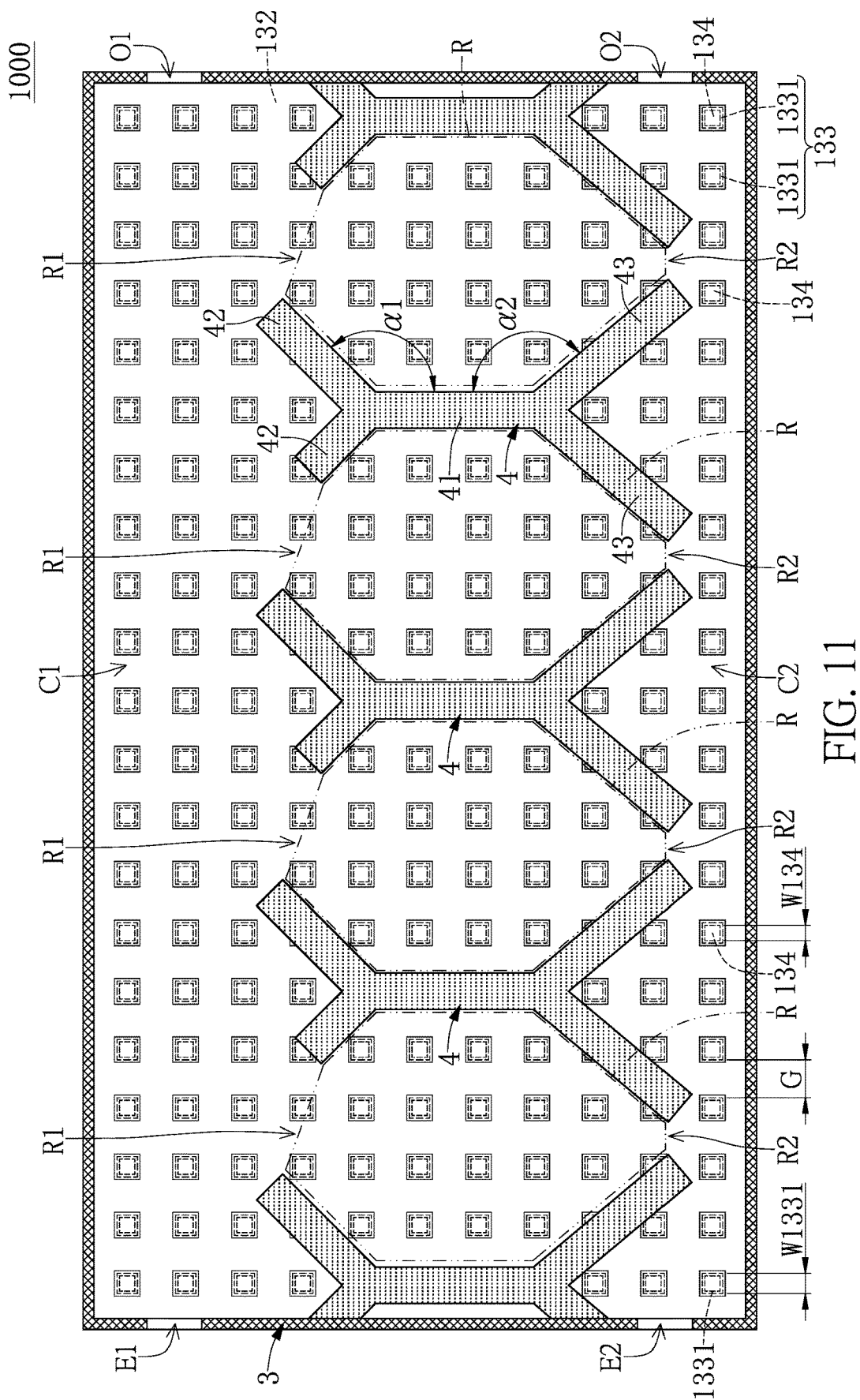
FIG. 11 is a cross-sectional view taken along line XI-XI of FIG. 9.

In the present embodiment, as shown in FIG. 9 and FIG. 10, the material of any one of the spacing walls 4 is a soft high bioaffinity material, such as thick film photoresist (e.g., SU-8), polydimethylsiloxane (PDMS), acrylic foam, or silicone. Each of the spacing walls 4 is located between and connected to the insulating layer 14 and the second electrode layer 22, so that the photodiode layer 13 (e.g., the triggering pads 1331) can be partially embedded in the spacing walls 4.

Moreover, as shown in FIG. 10 to FIG. 13, the spacing walls 4 are arranged in one row and are spaced apart from each other, and any two of the spacing walls 4 adjacent to each other have one of a plurality of culture regions R therebetween. Furthermore, a first flow channel C1 is arranged at one side of the row of the spacing walls 4 and is in spatial communication with each of the culture regions R, and a second flow channel C2 is arranged at another side of the row of the spacing walls 4 and is in spatial communication with each of the culture regions R.

Figure 12:
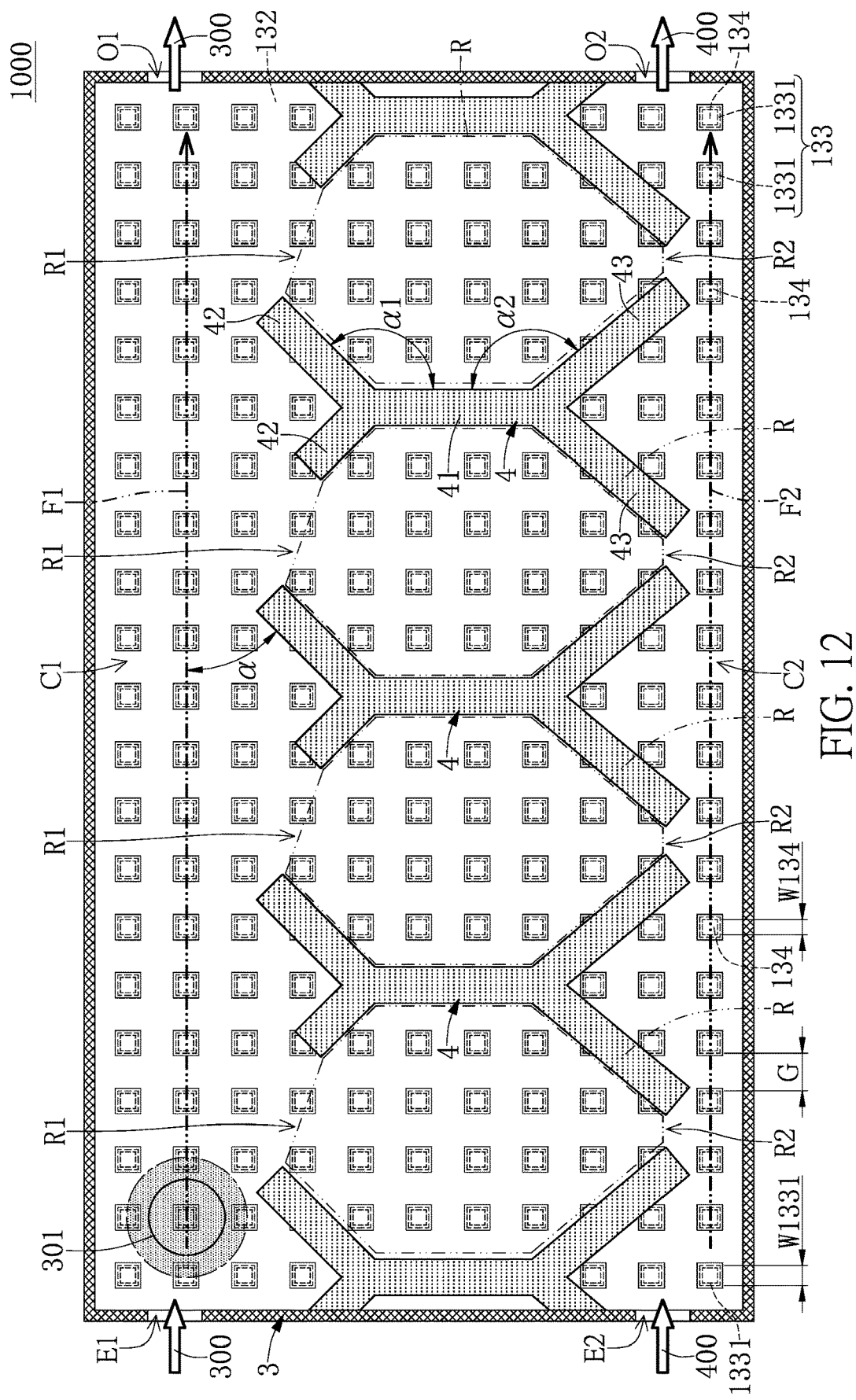
FIG. 12 and FIG. 13 are perspective cross-sectional views showing the biological particle selection apparatus of FIG. 11 used to be injected with the liquid specimen and a culture medium.
Figure 13:
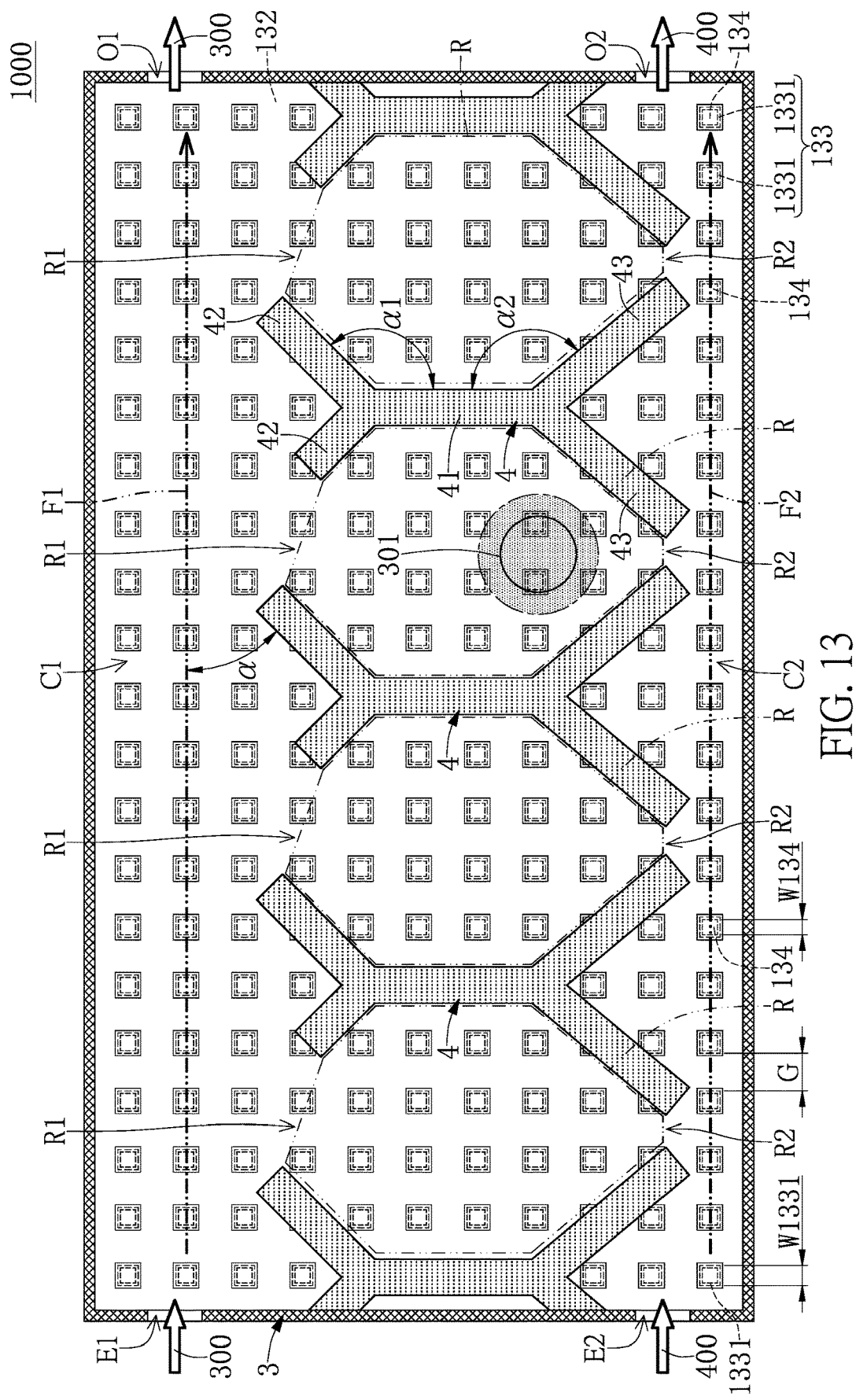

Specifically, when the first flow channel C1 is injected with the liquid specimen 300, the contactless selection device 100 allows a light source to irradiate light onto the photodiode layer 13 (e.g., an irradiated area surrounded by a dot-chain line shown in FIG. 12 and FIG. 13) so as to apply a DEP force on the target biological particle, so that the contactless selection device 100 can move the target biological particle 301 to one of the culture regions R by moving the light source, and movement of the target biological particle 301 is limited by the one of the culture regions R so as to prevent the target biological particle 301 from moving to the second flow channel C2.

Accordingly, the biological particle selection apparatus 1000 (or the contactless selection device 100) provided by the present embodiment has the spacing walls 4 for forming a dual-channel structure (e.g., the first flow channel C1 and the second flow channel C2) that is in spatial communication with each of the culture regions R, so that the target biological particle 301 can be moved into any one of the culture regions R from the first flow channel C1, and metabolites generated from the target biological particle 301 can be guided to the second flow channel C2, thereby effectively enhancing the culture or growth effect of the target biological particle 301.

Moreover, the triggering pads 1331 respectively arranged in the culture regions R have a specific structural design (e.g., any two of the triggering pads 1331 adjacent to each other are spaced apart by the distance G, and the width W1331 of each of the triggering pads 1331 is a predetermined value), thereby facilitating to stimulate the target biological particle 301 located in any one of the culture regions R.

It should be noted that at least one of the mating structure 2 and the bonding layer 3 has a first inlet E1 and a first outlet O1, which are respectively in spatial communication with two ends of the first flow channel C1, and at least one of the mating structure 2 and the bonding layer 3 has a second inlet E2 and a second outlet O2, which are respectively in spatial communication with two ends of the second flow channel C2.

In the present embodiment, the first flow channel C1 defines a first flowing direction F1 (e.g., a direction from the first inlet E1 to the first outlet O1), the second flow channel C2 defines a second flowing direction F2 that is preferably parallel to the first flowing direction F1, and a width of the second flow channel C2 is preferable less than a width of the first flow channel C1, but the present disclosure is not limited thereto. Moreover, the first inlet E1 is arranged adjacent to the second inlet E2, and the first outlet O1 is arranged adjacent to the second outlet O2.

Accordingly, the liquid specimen 300 can be injected into the contactless selection device 100 through the first inlet E1, and can flow out of the contactless selection device 100 through the first outlet O1. Moreover, a culture medium 400 can be injected into the contactless selection device 100 through the second inlet E2, and can flow out of the contactless selection device 100 through the second outlet O2.

Specifically, each of the culture regions R has a first opening R1 and a second opening R2. The first opening R1 is in spatial communication with the first flow channel C1, and the second opening R2 is in spatial communication with the second flow channel C2. The second opening R2 is smaller than the first opening R1, and a width of the second opening R2 is about 2 µm. In the accommodating space C of the contactless selection device 100, the first flow channel C1 is in spatial communication with the second flow channel C2 only through any one of the culture regions R.

The spacing walls 4 satisfying the above conditions can be provided in more than one configuration, and the following description of the present embodiment only describes the spacing walls 4 in a preferable one configuration, but the present disclosure is not limited thereto. Moreover, as the spacing walls 4 in the present embodiment are of the substantially same structure (e.g., the spacing walls 4 located at two ends of the row are slightly different from the others), the following description discloses the structure of just one of the spacing walls 4 for the sake of brevity, but the present disclosure is not limited thereto.

Specifically, the spacing wall 4 in the present embodiment includes an elongated partition segment 41, two first guiding segments 42 connected to one end of the partition segment 41, and two second guiding segments 43 that are connected to another end of the partition segment 41. The partition segment 41 is substantially perpendicular to the first flowing direction F1 (or the second flowing direction F2), a first angle α1 between the partition segment 41 and any one of the two first guiding segments 42 is within a range from 110 degrees to 160 degrees, a second angle α2 between the partition segment 41 and any one of the two second guiding segments 43 is within a range from 100 degrees to 160 degrees, and a length of any one of the second guiding segments 43 is greater than a length of any one of the first guiding segments 42, but the present disclosure is not limited thereto.

In other words, two of the first guiding segments 42 arranged adjacent to each other and respectively belonging to any two of the spacing walls 4 adjacent to each other jointly define the first opening R1, and two of the second guiding segments 43 arranged adjacent to each other and respectively belonging to any two of the spacing walls 4 adjacent to each other jointly define the second opening R2 that is smaller than the first opening R1, so that the target biological particle 301 can be moved along the first flow channel C1 and into one of the culture regions R through the corresponding first opening R1, and movement of the target biological particle 301 in the one of the culture regions R can be limited by the corresponding second opening R2 so as to prevent the target biological particle 301 from moving to the second flow channel C2.

Moreover, the two of the first guiding segments 42 defining the first opening R1 have different lengths, and a longer one of the two of the first guiding segments 42 is located at an upstream of the first flowing direction F1 and is configured to contact the liquid specimen 300 that flows along the first flowing direction F1 by an acute angle α within a range from 20 degrees to 70 degrees. Accordingly, the longer one of the two of the first guiding segments 42 can be configured to prevent cells in the liquid specimen 300 other than the target biological particle 301 from being accidentally moved into the corresponding culture region R.

It should be noted that in the contactless selection device 100, other structures being in cooperation with the spacing walls 4 can be adjusted or changed according to design requirements and are not limited by the first to third embodiments. For example, in other embodiments of the present disclosure not shown in the drawings, the photodiode layer 13 can be a structure other than a semiconductor layer in PIN-type.

Fifth Embodiment

Figure 14:
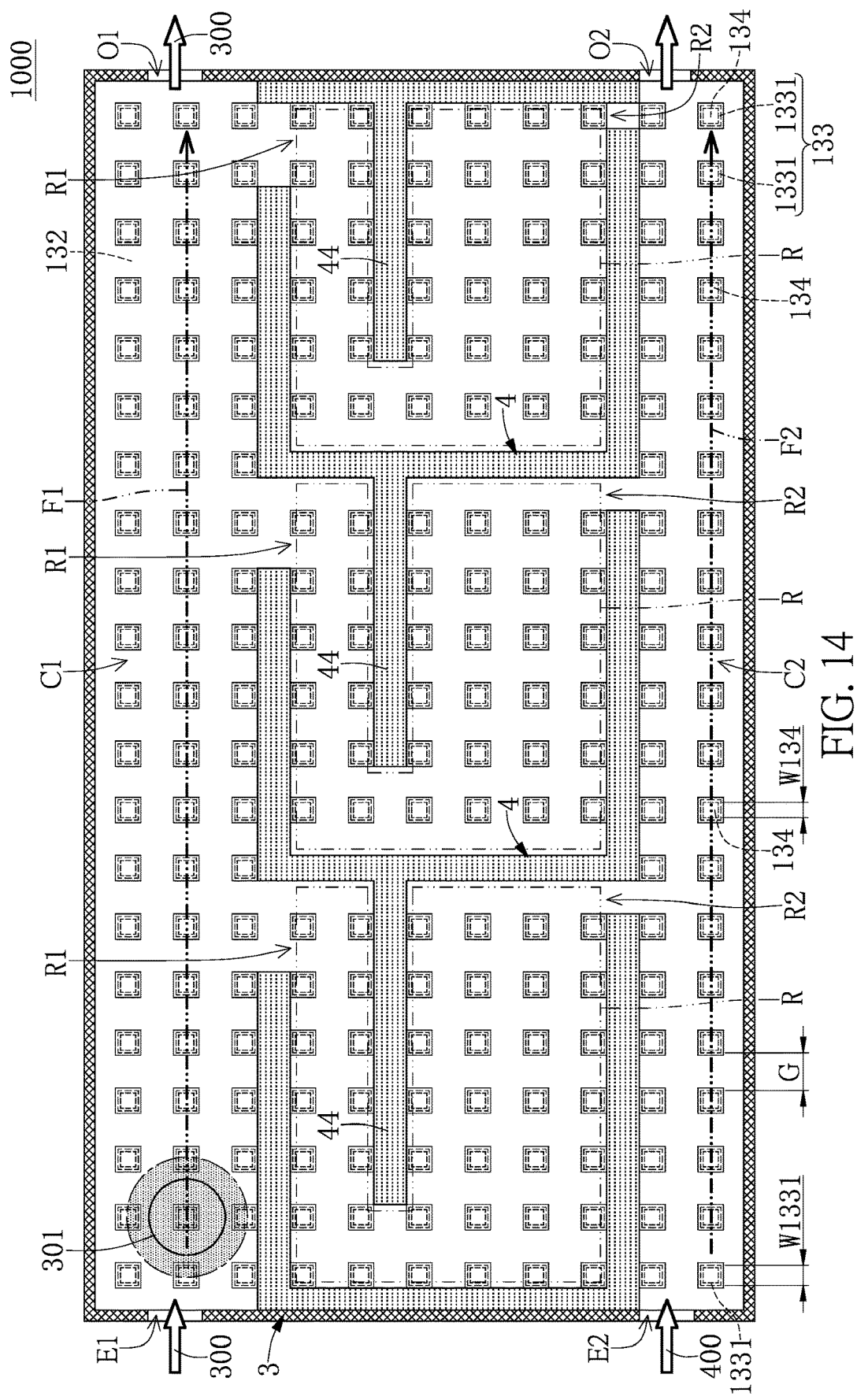
FIG. 14 is a cross-sectional view of the biological particle selection apparatus according to a fifth embodiment of the present disclosure.

Referring to FIG. 14, a fifth embodiment of the present disclosure is provided, which is similar to the fourth embodiment of the present disclosure. For the sake of brevity, descriptions of the same components in the fourth and fifth embodiments of the present disclosure will be omitted herein, and the following description only discloses different features between the fourth and fifth embodiments, in which the different features reside in the spacing walls 4.

In the present embodiment, at least one of any two of the spacing walls 4 adjacent to each other has a distribution segment 44 arranged in the corresponding culture region R, so that a flowing path of the liquid specimen 300 extends between the first opening R1 and the second opening R2, thereby preventing objects in the liquid specimen 300 other than the target biological particle 301 from being accidentally moved into the corresponding culture region R.

Sixth Embodiment

Figure 15:
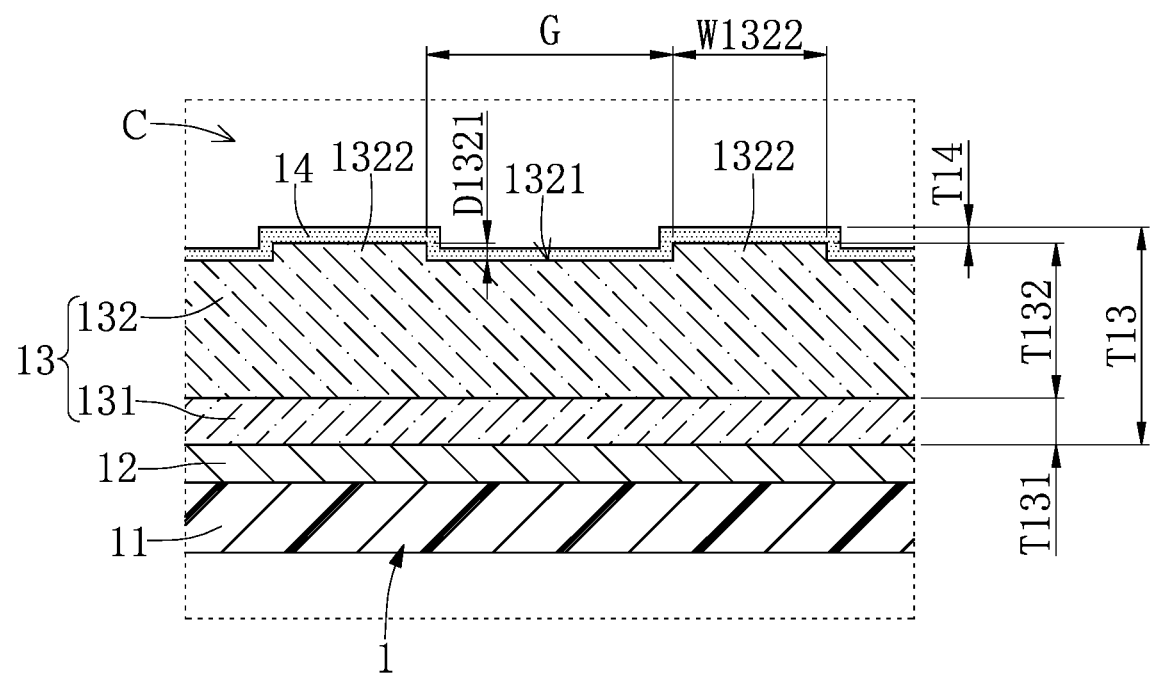
FIG. 15 is an enlarged view of the biological particle selection apparatus according to a sixth embodiment of the present disclosure.
Figure 16:
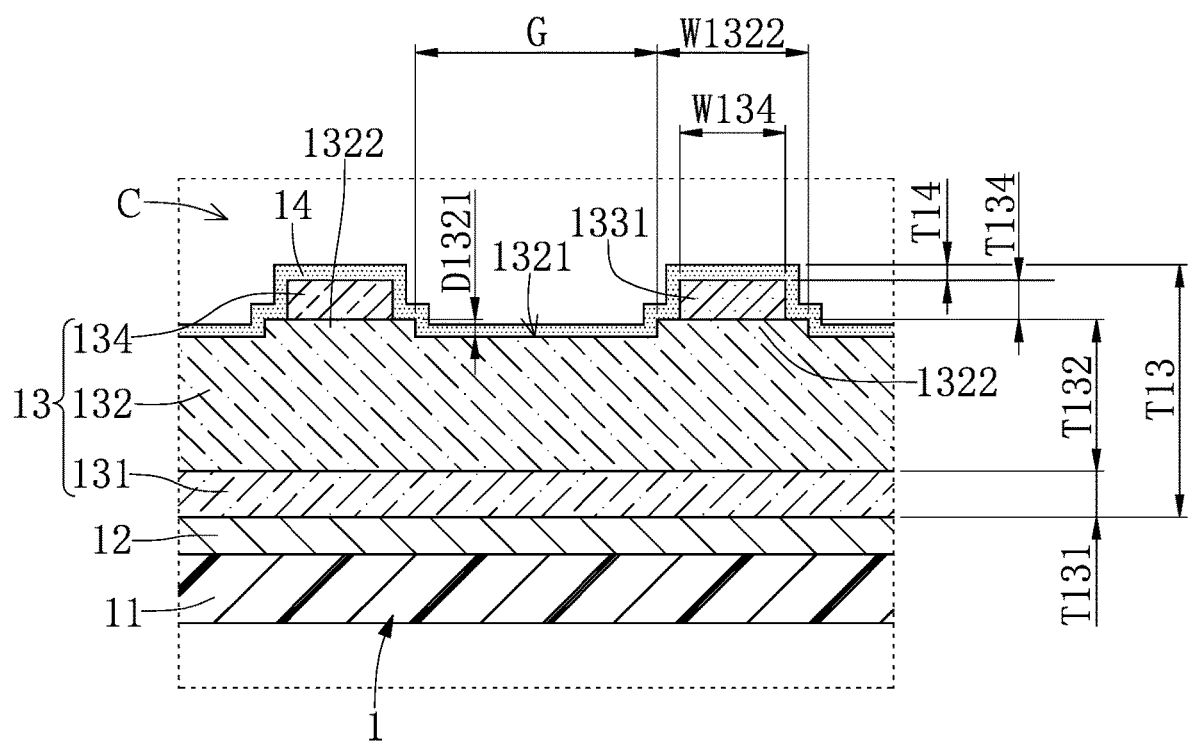
FIG. 16 is an enlarged view of the biological particle selection apparatus in another configuration according to the sixth embodiment of the present disclosure.

Referring to FIG. 15 and FIG. 16, a sixth embodiment of the present disclosure is provided, which is similar to the second embodiment of the present disclosure. For the sake of brevity, descriptions of the same components in the second and sixth embodiments of the present disclosure will be omitted herein, and the following description only discloses different features between the second and sixth embodiments, in which the different features reside in the photodiode layer 13.

In the present embodiment, as shown in FIG. 15, the photodiode layer 13 only includes the first doped layer 131 formed on the first electrode layer 12 and the I-type layer 132 that is formed on the first doped layer 131. The I-type layer 132 has a patterned trench 1321 recessed therein which forms a plurality of protruding stages 1322 spaced apart from each other. Specifically, a width W1322 (e.g., 5 μm) of each of the protruding stages 1322 is within a range from 3 μm to 7 μm, and a distance G (e.g., 1 μm) between any two of the protruding stages 1322 adjacent to each other is less than or equal to 2 μm.

Moreover, as shown in FIG. 16, the photodiode layer 13 can further include a plurality of transparent electrode pads 134 respectively formed on the protruding stages 1322, and the width W1322 of each of the protruding stages 1322 is greater than a width W134 (e.g., 3 μm) of the corresponding transparent electrode pad 134.

Beneficial Effects of the Embodiments

In conclusion, the photodiode layer of the biological particle selection apparatus (or the contactless selection device) provided by the present disclosure has a specific structural design (e.g., any two of the triggering pads or the protruding stages adjacent to each other are spaced apart by a distance, and the width of each of the triggering pads or the protruding stages is a predetermined value; or, the transparent electrode pads can be further formed on the triggering pads), so that any one of the triggering pads can be used to generate the concentrated electric field in a contactless photoelectric coupling manner that is similar to a corona discharge, thereby enabling to accurately move (or capture) the target biological particle to any position.

Moreover, the biological particle selection apparatus (or the contactless selection device) provided by the present disclosure has spacing walls for forming a dual-channel structure (e.g., the first flow channel and the second flow channel) that is in spatial communication with each of the culture regions, so that the target biological particle can be moved into any one of the culture regions from the first flow channel, and metabolites generated from the target biological particle can be guided to the second flow channel, thereby effectively enhancing the culture or growth effect of the target biological particle.

Specifically, the triggering pads respectively arranged in the culture regions have a specific structural design (e.g., any two of the triggering pads adjacent to each other are spaced apart by the distance, and the width of each of the triggering pads is a predetermined value), thereby facilitating to stimulate the target biological particle located in any one of the culture regions.

The foregoing description of the exemplary embodiments of the disclosure has been presented only for the purposes of illustration and description and is not intended to be exhaustive or to limit the disclosure to the precise forms disclosed. Many modifications and variations are possible in light of the above teaching.

The embodiments were chosen and described in order to explain the principles of the disclosure and their practical application so as to enable others skilled in the art to utilize the disclosure and various embodiments and with various modifications as are suited to the particular use contemplated. Alternative embodiments will become apparent to those skilled in the art to which the present disclosure pertains without departing from its spirit and scope.

What is claimed is:

1. A biological particle selection apparatus for selecting a target biological particle from a liquid specimen, comprising:
    a contactless selection device including:
        a light triggering structure including:
            a first substrate;
            a first electrode layer formed on the first substrate;
            a photodiode layer formed on the first electrode layer, wherein a thickness of the photodiode layer is within a range from 1 μm to 3 μm, and the photodiode layer includes:
                a first doped layer formed on the first electrode layer;
                an I-type layer formed on the first doped layer; and
                a second doped layer including a plurality of triggering pads that are formed on the I-type layer and that are spaced apart from each other, wherein a width of each of the triggering pads is within a range from 3 μm to 7 μm, and a distance between any two of the triggering pads adjacent to each other is less than or equal to 2 μm; and
            an insulating layer covering the photodiode layer; and
        a mating structure spaced apart from the light triggering structure, wherein at least one of the mating structure and the light triggering structure is transparent, and the mating structure includes a second substrate and a second electrode layer that is formed on the second substrate and that faces toward the light triggering structure; and
    an alternating current source electrically coupled to the first electrode layer and the second electrode layer;
    wherein, when the liquid specimen is located between the insulating layer and the second electrode layer of the contactless selection device, the contactless selection device allows a light source to irradiate light onto at least one of the triggering pads so as to generate a concentrated and non-uniform electric field to the liquid specimen for applying a dielectrophoresis (DEP) force on the target biological particle, and wherein the DEP force is capable of driving movement of the target biological particle.

2. The biological particle selection apparatus according to claim 1, wherein the photodiode layer includes a plurality of transparent electrode pads respectively formed on the triggering pads, and the width of each of the triggering pads is greater than a width of the corresponding transparent electrode pad.

3. The biological particle selection apparatus according to claim 2, wherein a thickness of each of the triggering pads is 3% to 10% of a thickness of the corresponding transparent electrode pad.

4. The biological particle selection apparatus according to claim 1, wherein the first doped layer covers at least 90% of an area of the first electrode layer, and the I-type layer covers an entirety of the first doped layer.

5. The biological particle selection apparatus according to claim 4, wherein the I-type layer has a patterned trench recessed therein which forms a plurality of protruding stages spaced apart from each other, and the triggering pads are respectively formed on the protruding stages.

6. The biological particle selection apparatus according to claim 5, wherein an edge of each of the triggering pads is flush with an edge of the corresponding protruding stage, and a depth of the patterned trench is 1% to 5% of a thickness of the I-type layer.

7. The biological particle selection apparatus according to claim 1, wherein the I-type layer includes a plurality of I-type pads that are disposed on the first doped layer and that are spaced apart from each other, and wherein the triggering pads are respectively formed on the I-type pads, and the width of each of the triggering pads is less than a width of the corresponding I-type pad.

8. The biological particle selection apparatus according to claim 7, wherein the first doped layer includes a plurality of spacing pads that are disposed on the first electrode layer and that are spaced apart from each other, and wherein the I-type pads are respectively formed on the spacing pads, and an edge of each of the I-type pads is flush with an edge of the corresponding spacing pad.

9. The biological particle selection apparatus according to claim 1, wherein a thickness of each of the triggering pads and a thickness of the first doped layer are each 1% to 5% of a thickness of the I-type layer, and the thickness of each of the triggering pads is less than the thickness of the first doped layer.

10. The biological particle selection apparatus according to claim 1, wherein the contactless selection device includes:
a bonding layer connected to and located between the light triggering structure and the mating structure, wherein the bonding layer, the light triggering structure, and the mating structure jointly define an accommodating space that accommodates the photodiode layer therein; and
a plurality of spacing walls located in the accommodating space and connected to the light triggering structure and the mating structure, wherein the spacing walls are arranged in one row and are spaced apart from each other, and any two of the spacing walls adjacent to each other have one of a plurality of culture regions therebetween, and wherein a first flow channel is arranged at one side of the row of the spacing walls and is in spatial communication with each of the culture regions, and a second flow channel is arranged at another side of the row of the spacing walls and is in spatial communication with each of the culture regions;
wherein, when the first flow channel is injected with the liquid specimen, the contactless selection device is configured to move the target biological particle to one of the culture regions by moving the light source, and the movement of the target biological particle is limited by the one of the culture regions so as to prevent the target biological particle from moving to the second flow channel.

11. The biological particle selection apparatus according to claim 10, wherein the triggering pads are partially embedded in the spacing walls, and each of the spacing walls includes:
a partition segment;
two first guiding segments connected to one end of the partition segment, wherein a first angle between the partition segment and any one of the two first guiding segments is within a range from 110 degrees to 160 degrees; and
two second guiding segments connected to another end of the partition segment, wherein a second angle between the partition segment and any one of the two second guiding segments is within a range from 100 degrees to 160 degrees;
wherein two of the first guiding segments arranged adjacent to each other and respectively belonging to two of the spacing walls adjacent to each other jointly define a first opening, and two of the second guiding segments arranged adjacent to each other and respectively belonging to two of the spacing walls adjacent to each other jointly define a second opening that is smaller than the first opening.

12. The biological particle selection apparatus according to claim 11, wherein the first flow channel defines a first flowing direction and allows the liquid specimen to flow along the first flowing direction, wherein the two of the first guiding segments defining the first opening have different lengths, and a longer one of the two of the first guiding segments is located at an upstream of the first flowing direction and is configured to contact the liquid specimen by an acute angle within a range from 20 degrees to 70 degrees.

13. The biological particle selection apparatus according to claim 10, wherein each of the culture regions has a first opening and a second opening, wherein, in each of the culture regions, the first opening is in spatial communication with the first flow channel, and the second opening that is in spatial communication with the second flow channel and is smaller than the first opening, and wherein in the accommodating space of the contactless selection device, the first flow channel is in spatial communication with the second flow channel only through any one of the culture regions.

14. The biological particle selection apparatus according to claim 13, wherein at least one of the any two of the spacing walls adjacent to each other has a distribution segment arranged in the corresponding culture region, so that a flowing path of the liquid specimen extends between the first opening and the second opening of the corresponding culture region.

15. A contactless selection device for selecting a target biological particle from a liquid specimen, comprising:
a light triggering structure including:
a first substrate;
a first electrode layer formed on the first substrate;
a photodiode layer formed on the first electrode layer, wherein a thickness of the photodiode layer is within a range from 1 µm to 3 µm, and the photodiode layer includes:
a first doped layer formed on the first electrode layer;
an I-type layer formed on the first doped layer; and
a second doped layer including a plurality of triggering pads that are formed on the I-type layer and that are spaced apart from each other, wherein a width of each of the triggering pads is within a range from 3 µm to 7 µm, and a distance between any two of the triggering pads adjacent to each other is less than or equal to 2 µm; and
an insulating layer covering the photodiode layer; and
a mating structure spaced apart from the light triggering structure, wherein at least one of the mating structure and the light triggering structure is transparent, and the mating structure includes a second substrate and a second electrode layer that is formed on the second substrate and that faces toward the light triggering structure;
wherein a space between the insulating layer and the second electrode layer of the contactless selection device is configured to accommodate the liquid specimen so as to implement a selection process for the target biological particle.

16. The contactless selection device according to claim 15, wherein the photodiode layer includes a plurality of transparent electrode pads respectively formed on the triggering pads, the width of each of the triggering pads is greater than a width of the corresponding transparent electrode pad, and a thickness of each of the triggering pads is 3% to 10% of a thickness of the corresponding transparent electrode pad.

17. The contactless selection device according to claim 16, wherein a thickness of each of the triggering pads and a thickness of the first doped layer are each 1% to 5% of a thickness of the I-type layer, and the thickness of each of the triggering pads is less than the thickness of the first doped layer.

18. The contactless selection device according to claim 15, further comprising:
- a bonding layer connected to and located between the light triggering structure and the mating structure, wherein the bonding layer, the light triggering structure, and the mating structure jointly define an accommodating space that accommodates the photodiode layer therein; and
- a plurality of spacing walls located in the accommodating space and connected to the light triggering structure and the mating structure, wherein the spacing walls are arranged in one row and are spaced apart from each other, and any two of the spacing walls adjacent to each other have one of a plurality of culture regions therebetween, and wherein a first flow channel is arranged at one side of the row of the spacing walls and is in spatial communication with the culture regions, and a second flow channel is arranged at another side of the row of the spacing walls and is in spatial communication with the culture regions;
- wherein in the accommodating space of the contactless selection device, the first flow channel is in spatial communication with the second flow channel only through any one of the culture regions.

19. A light triggering structure of a contactless selection device, comprising:
- a first substrate;
- a first electrode layer formed on the first substrate;
- a photodiode layer formed on the first electrode layer, wherein a thickness of the photodiode layer is within a range from 1 μm to 3 μm, and the photodiode layer includes:
  - a first doped layer formed on the first electrode layer; and
  - an I-type layer formed on the first doped layer, wherein the I-type layer has a patterned trench recessed therein which forms a plurality of protruding stages spaced apart from each other, and wherein a width of each of the protruding stages is within a range from 3 μm to 7 μm, and a distance between any two of the protruding stages adjacent to each other is less than or equal to 2 μm; and
- an insulating layer covering the photodiode layer.

20. The light triggering structure according to claim 19, wherein the photodiode layer includes a plurality of transparent electrode pads respectively formed on the protruding stages, and the width of each of the protruding stages is greater than a width of the corresponding transparent electrode pad.

* * * * *